United States Patent
Kondo et al.

(10) Patent No.: US 7,801,336 B2
(45) Date of Patent: *Sep. 21, 2010

(54) LIVING EYE JUDGING METHOD AND LIVING EYE JUDGING DEVICE

(75) Inventors: Kenji Kondo, Kyoto (JP); Takeo Azuma, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/390,705

(22) Filed: Feb. 23, 2009

(65) Prior Publication Data

US 2009/0161923 A1    Jun. 25, 2009

Related U.S. Application Data

(63) Continuation of application No. 10/540,060, filed as application No. PCT/JP2004/009698 on Jul. 1, 2004.

(30) Foreign Application Priority Data

Jul. 4, 2003    (JP) .............................. 2003-192268

(51) Int. Cl.
*G06K 9/00* (2006.01)
(52) U.S. Cl. ...................................................... 382/117
(58) Field of Classification Search ................... 382/117
See application file for complete search history.

(56) References Cited

U.S. PATENT DOCUMENTS

| | | | |
|---|---|---|---|
| 4,641,349 A | 2/1987 | Flom et al. ..................... 382/2 |
| 4,834,528 A | 5/1989 | Howland et al. | |
| 5,016,282 A | 5/1991 | Tomono et al. ............. 382/117 |
| 5,231,674 A * | 7/1993 | Cleveland et al. ........... 382/117 |
| 5,291,560 A | 3/1994 | Daugman .................... 382/117 |
| 5,719,950 A | 2/1998 | Osten et al. ................. 382/115 |
| 6,028,949 A | 2/2000 | McKendall .................. 382/117 |
| 6,134,339 A * | 10/2000 | Luo ............................ 382/115 |
| 6,307,954 B1 | 10/2001 | Suzaki ........................ 382/117 |
| 6,542,624 B1* | 4/2003 | Oda ............................ 382/117 |
| 6,546,121 B1 | 4/2003 | Oda ............................ 382/117 |
| 6,785,406 B1* | 8/2004 | Kamada ...................... 382/117 |
| 6,853,854 B1* | 2/2005 | Proniewicz et al. ......... 600/319 |
| 2003/0012413 A1 | 1/2003 | Kusakari et al. ............. 382/117 |
| 2004/0184670 A1 | 9/2004 | Jarman et al. ............... 382/274 |

FOREIGN PATENT DOCUMENTS

| | | |
|---|---|---|
| FR | 2587191 A | 3/1987 |
| JP | 05-084166 | 12/1993 |

(Continued)

*Primary Examiner*—Vu Le
*Assistant Examiner*—Michael Vanchy, Jr.
(74) *Attorney, Agent, or Firm*—Harness, Dickey & Pierce, P.L.C.

(57) ABSTRACT

An eye (EY) of a person to be shot is illuminated coaxially with the optical axis of a camera (11), and then, is shot. At this time, a retinal reflex is caused and the luminance in the pupil region becomes high if the eye (EY) is a living eye. A living eye judgment section (17) judges whether an eye included in the image is a living eye is performed based on the luminance in the pupil region of the image captured by the camera (11).

7 Claims, 14 Drawing Sheets

FOREIGN PATENT DOCUMENTS

| | | |
|---|---|---|
| JP | 10-137220 | 5/1998 |
| JP | 2000-033080 | 2/2000 |
| JP | 2000-105830 | 4/2000 |
| JP | 3271750 B2 | 1/2002 |
| JP | 3307936 | 5/2002 |
| JP | 3315648 | 6/2002 |
| JP | 2002-312772 | 10/2002 |
| JP | 2003-030659 | 1/2003 |
| JP | 2003-331268 A | 11/2003 |
| JP | 2004-171350 A | 6/2004 |
| WO | 87/01571 A1 | 3/1987 |
| WO | 94/09446 | 4/1994 |

* cited by examiner

<Real eye shot>

Luminance in iris region
Average: I1

Luminance in pupil region
Average: P1
Standard deviation: σ1

(Except luminance saturated region)

<Printer output shot>

Luminance in iris region
Average: I2

Luminance in pupil region
Average: P2
Standard deviation: σ2

<Real eye shot>

Luminance in iris region
Average: I3

Luminance in pupil region
Average: P3
Standard deviation: σ3
(Except luminance saturated region)

<Printer output shot>

Luminance in iris region
Average: I4

Luminance in pupil region
Average: P4
Standard deviation: σ4

LIVING EYE JUDGING METHOD AND LIVING EYE JUDGING DEVICE

CROSS-REFERENCE TO RELATED APPLICATION

This application is a continuation of U.S. patent application Ser. No. 10/540,060 filed on Jun. 22, 2005. The entire disclosure of the above application is incorporated herein by reference.

TECHNICAL FIELD

The present invention relates to generally called a living eye judgment for judging whether an eye included in an image is a living eye or not for preventing false authentication of one which is not a living eye, for example, in iris authentication.

BACKGROUND ART

In recent years, a personal authentication technique utilizing iris images has been started to be used for entrance/exit management in a restricted building, bank ATMs (Automated Teller Machines), PC login applications, and the like. Especially, the method disclosed in Patent Document 1 has already gone commercial in all over the world and is becoming a de facto standard method.

In the method disclosed in Patent Document 1, an iris region is cut out from an image obtained by shooting the iris, the iris region is expressed in a polar coordinate, and then, 2D Gobor Wavelet filtering is performed to generate an iris code. Then, personal authentication is performed by comparing the thus generated iris code with an iris code registered in advance.

In personal authentication using iris images, there is a possibility of false authentication of a photograph of an iris or a counterfeit eye. Techniques for preventing such false authentication are disclosed in Patent Documents 2 and 3. In Patent Document 2, blinking of an eye or change in pupil diameter is detected. In Patent Document 3, change in pupil diameter is observed while applying stimulation by visible light.

(Patent Document 1) Japanese Patent No. 3307936B (Patent Document 2) Japanese Patent Application Laid Open Publication No. 2000-105830A (Patent Document 3) Japanese Patent No. 3315648B

PROBLEMS THAT THE INVENTION IS TO SOLVE

However, the conventional techniques involve the following problems.

Referring first to Patent Document 2, high speed shutters are necessary and it takes long processing time. In Patent Document 3, considerable time for processing is required because change in pupil diameter is observed.

The present invention has been made in view of the above problems and has its object of enabling discrimination between a living eye and a photograph or a counterfeit eye by a simple method.

SUMMARY OF THE INVENTION

The present invention utilizes a phenomenon called a retinal reflex. The retinal reflex will be explained briefly.

FIG. 1 is a section of an eyeball and shows the mechanism of the retinal reflex. In the retinal reflex as shown in FIG. 1, light passes through a pupil (a region that is not covered with an iris) is made incident, and then, is reflected on a retina. The reflected light, of which direction accords substantially with and is reverse to the incident light, passes through the pupil to get out of the eyeball. Consequently, the entire pupil looks bright in an image of an eye.

FIG. 2(a) is a schematic view of an eye image upon the retinal reflex and FIG. 2(b) is a graph showing a luminance profile on the horizontal line L in the image of FIG. 2(a). FIG. 2(b) indicates high luminance in the pupil region.

The retinal reflex as above is an inherent phenomena in an eye of a living body, and is neither caused in a printed image nor a counterfeit eye. The present invention has been made in this point of view.

Specifically, in order to solve the above problems, in the present invention, judgment as to whether an eye in the image is a living eye or not is performed, using an image obtained by shooting a subject with illumination coaxial with an optical axis of a camera, based on the luminance in the pupil region of the eye included in the image.

According to the present invention, the pupil region in an image obtained by shooting a living eye with illumination coaxial with the optical axis of the camera has high luminance by the retinal reflex. On the other hand, no retinal reflex is caused in a photograph, a printed imaged and a counterfeit eye, so that the luminance in the pupil region is not so high as that in a living eye. In this connection, judgment as to whether an eye included in an image is a living eye or not can be performed easily based on the luminance of the pupil region in the image.

Further, in the present invention, judgment as to whether eyes included in images is a living eye or not is performed, using a first image obtained by shooting a subject with illumination coaxial with an optical axis of a camera and a second image obtained by shooting the subject with illumination of which optical axis is different from the optical axis of the camera, based on luminance in the pupil regions of the eyes included in the first and second images.

In this invention, in a case of a living eye, the luminance in the pupil region is high because of the retinal reflex in the first image obtained by shooting the subject with illumination coaxial with the optical axis of the camera and the luminance in the pupil region is low in the second image obtained by shooting the subject with illumination of which optical axis is different from the optical axis of the camera. In short, a large difference is present in the pupil region between the first and second images. On the other hand, in a photograph, a printed image and a counterfeit eye, not so large difference in luminance is present between the pupil regions of the first and second images as in the living eye. Accordingly, the judgment as to whether the eyes included in the images are a living eye or not can be performed easily based on the luminance of the pupil regions in the images. Further, no luminance difference is present between the first and second images even in the case using a photograph and a printed image including an eye upon the retinal reflex, and therefore, accurate judgment is attained.

BEST MODE FOR CARRYING OUT THE INVENTION

Figure 1:
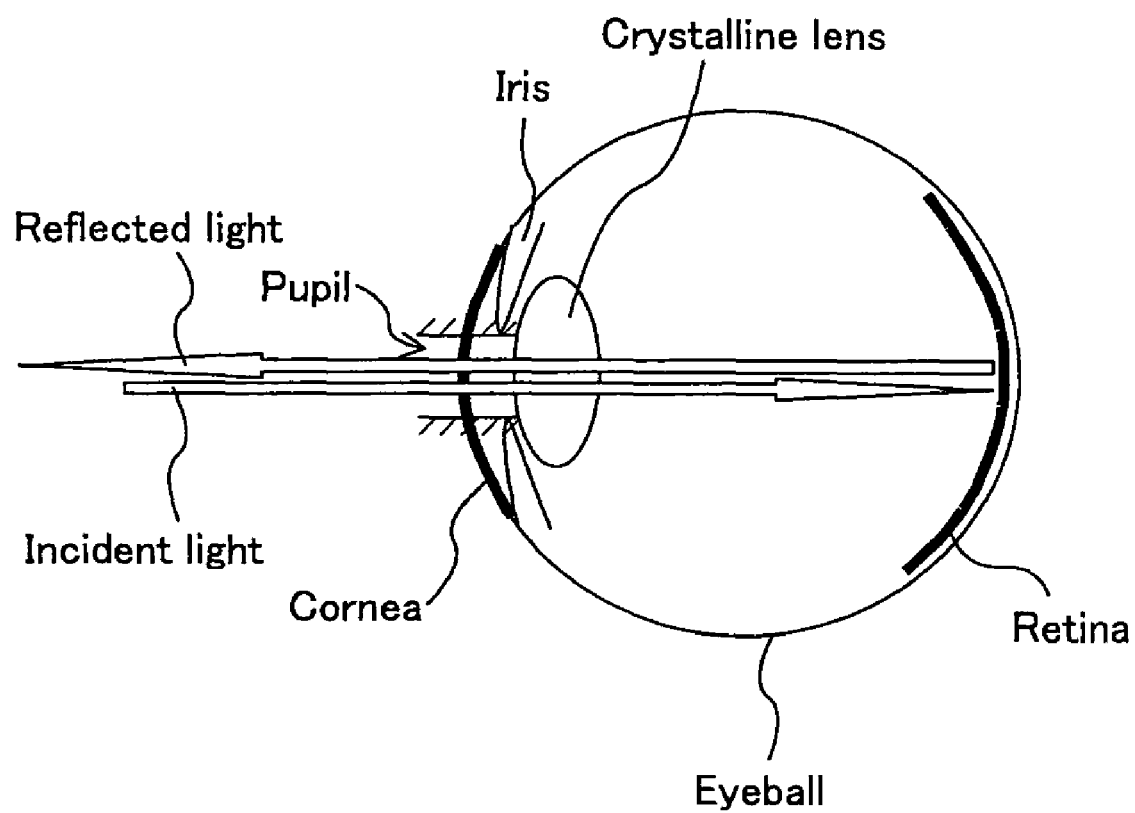
FIG. 1 is a section of an eyeball for illustrating a mechanism of a retinal reflex.

The first aspect of the present invention provides a living eye judging method including: a first step of obtaining an image captured by shooting a subject with illumination coaxial with an optical axis of a camera; and a second step of judging whether an eye included in the image is a living eye or not based on luminance in a pupil region of the eye in the image.

The second aspect of the present invention provides the living eye judging method of the first aspect, wherein in the second step, the eye is judged as a living eye when a difference in luminance between in the pupil region and in an iris region or a luminance ratio of the pupil region to the iris region is larger than a threshold value.

The third aspect of the present invention provides the living eye judging method of the first aspect, wherein in the first step, a plurality of images sequential in time are obtained, and in the second step, whether the eye is a living eye or not is judged based on time variation in a predetermined index for luminance in the pupil region obtained from the plurality of images.

The fourth aspect of the present invention provides the living eye judging method of the third aspect, wherein the predetermined index is an average value of luminance in the pupil region.

The fifth aspect of the present invention provides the living eye judging method of the third aspect, wherein the predetermined index is a ratio of luminance of the pupil region to the iris region.

The sixth aspect of the present invention provide the living eye judging method of third aspect, wherein the predetermined index is a total sum of luminance values of each pixel in the pupil region.

The seventh aspect of the present invention provides the living eye judging method of the sixth aspect, wherein the total sum of the luminance values is normalized by an area of the iris region.

The eighth aspect of the present invention provides a living eye judging method including: a first step of obtaining a first image captured by shooting a subject with illumination coaxial with an optical axis of a camera and a second image captured by shooting the subject with illumination having an optical axis different from the optical axis of the camera; and a second step of judging whether an eye included in the first and second images is a living eye or not based on luminance in pupil regions of the eye in the first and second images.

The ninth aspect of the present invention provides the living eye judging method of the eighth aspect, wherein the second step includes the steps of: obtaining a first luminance difference, which is a difference in luminance between the pupil region and an iris region in the first image, and a second difference, which is a difference in luminance between the pupil region and an iris region in the second image; and judging the eye as a living eye when an absolute value of a difference between the first luminance difference and the second luminance difference is larger than a predetermined threshold value.

The tenth aspect of the present invention provides the living eye judging method of the eight aspect, wherein the second step includes the steps of: obtaining a first luminance ratio, which is a ratio in luminance of the pupil region to an iris region in the first image, and a second luminance ratio, which is a ratio in luminance of the pupil region to an iris region in the second image; and judging the eye as a living eye when a ratio of the first luminance ratio to the second luminance ratio is larger than a predetermined threshold value.

The eleventh aspect of the present invention provides a living eye judging device including: a camera for shooting a subject; an illumination section for illuminating the subject coaxially with an optical axis of the camera; and a living eye judgment section that receives an image captured by the camera with illumination by the illumination section and performs judgment as to whether an eye included in the image is a living eye or not based on luminance in a pupil region of the eye in the image.

The twelfth aspect of the present invention provides a living eye judging device including: a camera for shooting a subject; a first illumination section for illuminating the subject coaxially with an optical axis of the camera; a second illumination section for illuminating the subject on an optical axis different from the optical axis of the camera; and a living eye judgment section that receives a first image captured by the camera with illumination by the first illumination section and a second image captured by the camera with illumination by the second illumination section and performs judgment as to whether an eye included in the first and second images is a living eye or not based on luminance in pupil regions of the eye in the first and second images.

The embodiments of the present invention will be described below with reference to the drawings.

FIRST EMBODIMENT

Figure 4:
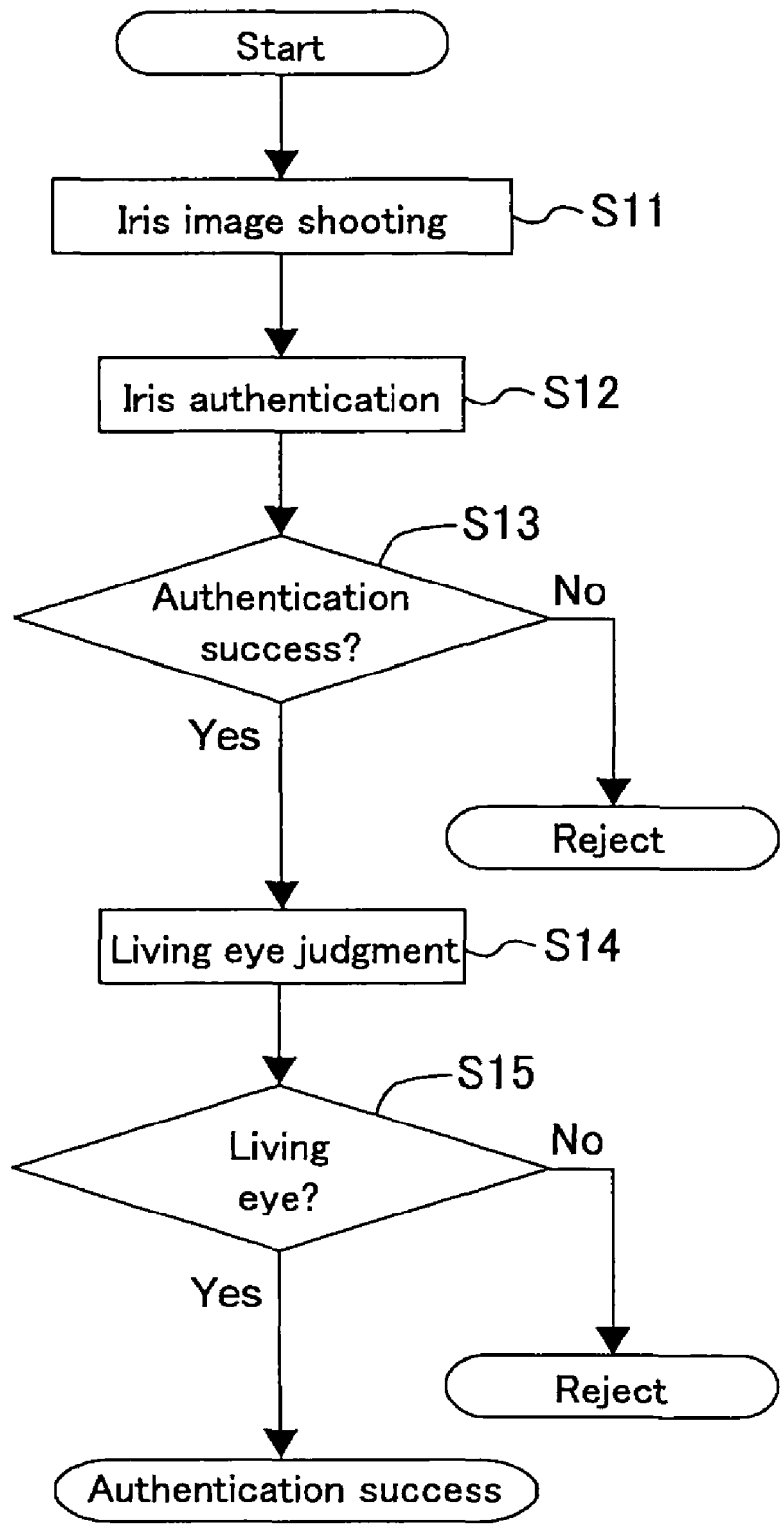
FIG. 4 is a flowchart showing an iris authentication method including living eye judgment according to each embodiment of the present invention.

FIG. 4 is a flowchart showing an iris authentication method according to the first embodiment of the present invention. The flow of FIG. 4 includes steps S14 and S15 of performing living eye judgment.

Figure 5:
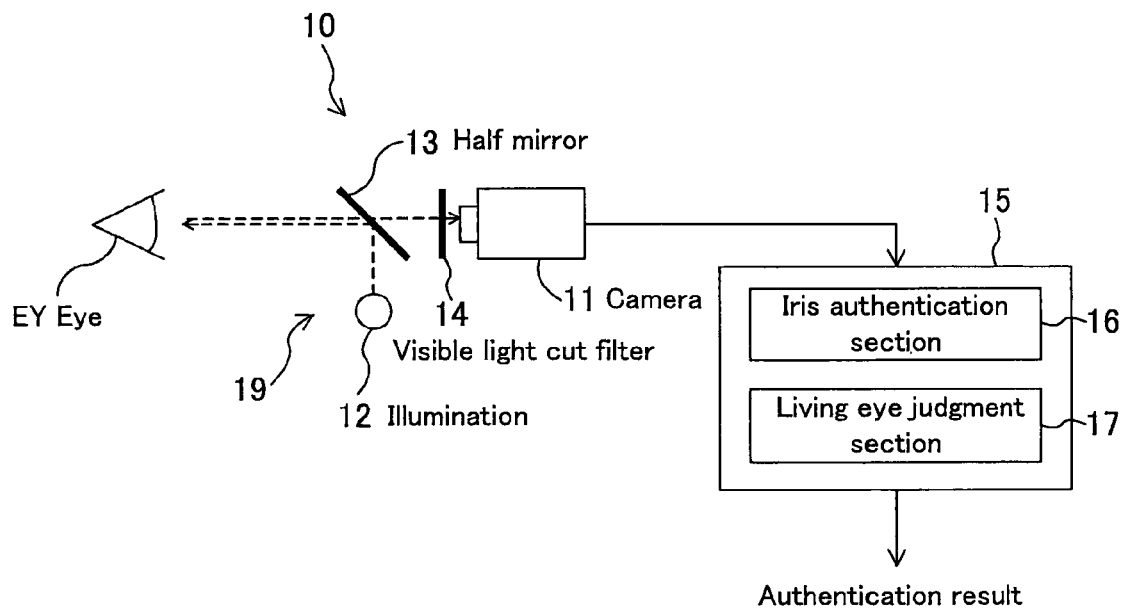
FIG. 5 shows one example of a constitution of an iris authentication device including a living eye judging device according to the first embodiment of the present invention.

FIG. 5 shows one example of the constitution of an iris authentication device according to the present embodiment. In FIG. 5, a shooting device 10 is provided with a camera 11 for shooting an eye EY (a subject) of a person to be shot, an illumination 12 and a half mirror 13. Light emitted from the illumination 12 is reflected on the half mirror 13 to illuminate the eye EY. The camera 11 captures an image of the eye EY through the half mirror 13 when the subject is illuminated by the illumination 12. At this time, the optical axis of the camera 11 is coaxial with that of the illumination 12 (coaxial incident illumination). In this way, the illumination 12 and the half mirror 13 composes illumination means 19. An image processing section 15 is provided with an iris authentication section 16 and a living eye judgment section 17 for performing iris authentication including living eye judgment on an eye image captured by the shooting device 10. The shooting device 10 and the living eye judgment section 17 compose a living eye judging device.

Figure 6:
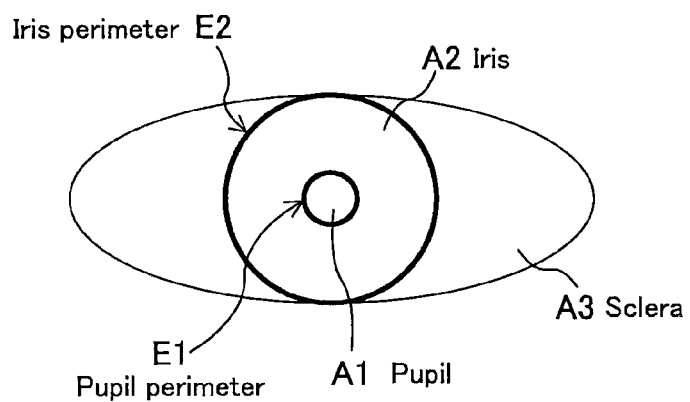
FIG. 6 is a front view illustrating a structure of an eye.

First, in a step S11, the shooting device 10 captures an iris image. As shown in FIG. 6, an eye is constituted by a pupil A1, an iris A2 and a sclera A3 when viewed from the front. The boundary between the pupil A1 and the iris A2 is called a pupil perimeter E1 and the boundary between the iris A2 and the sclera A3 is called an iris perimeter E2. In the step S11, shooting is performed so that at least the iris A2 is included in an image.

The illumination 12 of the shooting device 11 is composed of, for example, one or a plurality of LEDs having a waveform region of near-infrared. The advantages obtained by illuminating the eye EY using the near-infrared ray is that a person to be shot feels no glare.

Further, a visible light cut filter 14 is provided in front of the camera 11 because a captured image is used for iris authentication. With this filter, the camera 11 receives light of which component is only near-infrared.

It is noted that LEDs having the wavelength region of near-infrared is used as a light source in the present embodiment, but another light source or another wavelength region (e.g., visible light) may be used.

At shooting, the illumination 12 emits light in synchronization with only exposure of the camera 11. In so doing, a burden on a person to be shot caused by applying illumination to his/her eyes can be mitigated.

Next, in a step S12, iris authentication is performed on the image obtained in the step S11. The iris authentication section 16 executes this processing. Any methods for the iris authentication may be used, wherein the method disclosed in Patent Reference 1 is employed here. The schematic method is as follows.

(1) Determine the pupil perimeter E1 and the iris perimeter E2 to cut out the iris region.

(2) Transform the cut out iris region from an xy rectangular coordinate system to a rθ polar coordinate system.

(3) Determine an analysis band (by concentrically dividing the iris region into 8 rings).

(4) Apply multi-scale 2-d Gabor filter and binarize a Gabor-filtered signal to generate an iris code.

(5) Compare (exclusive OR) an iris code registered in advance with an iris code generated at the time of authentication to calculate the hamming distance between the two compared codes.

(6) If the hamming distance is shorter than a threshold value, accept the person to be authenticated as a registrant but otherwise reject as a non-registrant.

Then, in a step S13, whether the authentication has succeeded or not is checked. In the above item (6), if the person to be authenticated is accepted as a registrant, the authentication has succeeded (Yes) and the routine proceeds to a step S14. Otherwise (No), the person to be authenticated is rejected as a non-registrant and the processing terminates.

In the step S14, living eye judgment is performed. The living eye judgment section 17 executes this processing, which will be described later. When the judgment results in that the eye included in the image is not a living eye (No in S15), the person to be authenticated is rejected and the processing terminates. On the other hand, when the judgment results in that the eye included in the image is a living eye (Yes in S15), the processing terminates as authentication success.

Figure 7:
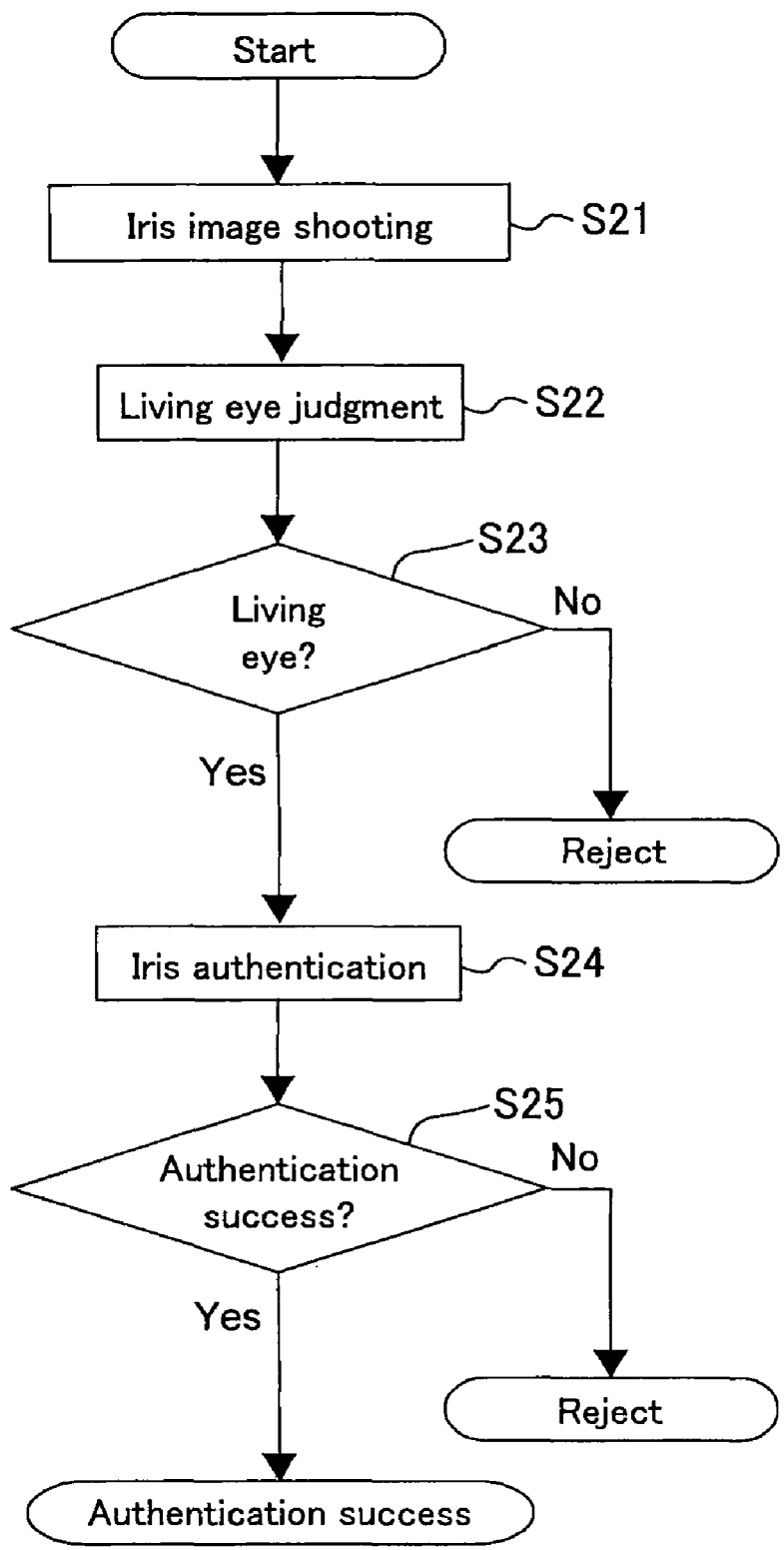
FIG. 7 is a flowchart showing another example of the iris authentication method including eye judgment according to each embodiment of the present invention.

It is noted that the iris authentication is performed first, and then, the living eye judgment is performed only after authentication success in the flow of FIG. 4. However, as shown in FIG. 7, it is possible that the living eye judgment is performed first (S22), and then, the iris authentication is performed (S24) only when the image is judged as an image of a living eye (Yes in S23). For final authentication, the image must not be rejected in both the living eye judgment and the iris authentication in either course.

Herein, the living eye judgment in the step S14 will be described along the flow of FIG. 8. The processing herein corresponds to the living eye judging method according to the present embodiment.

First, in a step S31, a pupil region is determined. Herein, in the case where the iris authentication S12 is performed before the living eye judgment S14 as in the flow of FIG. 4, the position of the pupil has been already obtained through the iris authentication, and accordingly, the result thereof can be utilized. On the other hand, in the case where the living eye judgment S22 is performed before the iris authentication S24 as in the flow of FIG. 7, the pupil region is determined at this time. Any optional methods may be employed for the pupil region determination. For example, the method disclosed in Patent Document 1 may be employed.

Figure 2:
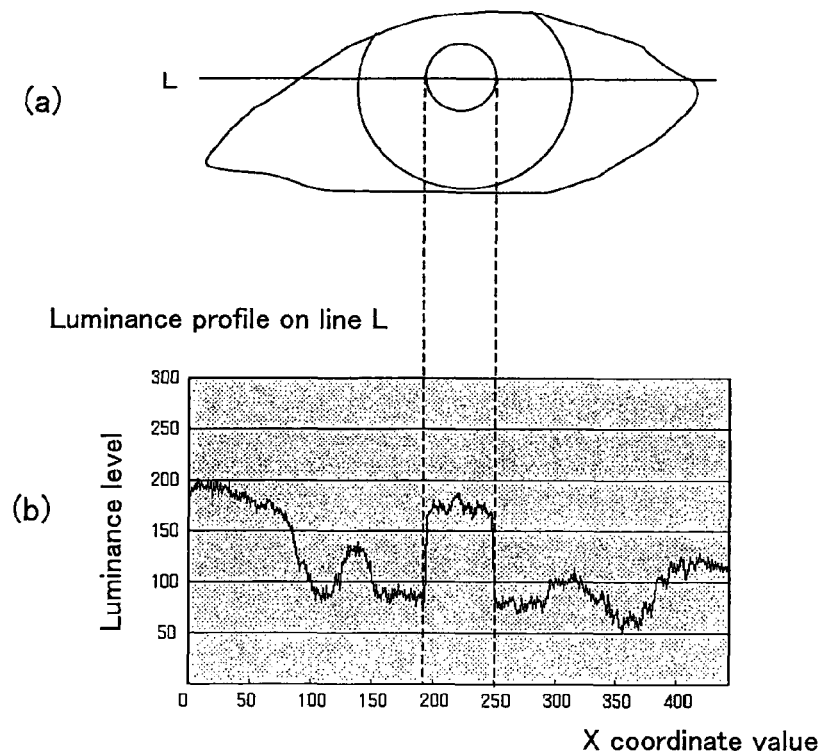
FIG. 2(a) is an image of an eye upon the retinal reflex and FIG. 2(b) is a graph showing luminance distribution in the image of FIG. 2(a).

Next, in a step S32, judgment is performed as to whether the eye included in the image is a living eye or not, based on the luminance in the pupil region. In the case of shooting with the use of the coaxial incident illumination as in the present embodiment, the luminance in the pupil region as a whole in the image including a living eye is high because of the retinal reflex as shown in FIG. 2(a). To the contrary, no retinal reflex is caused in the image including a photograph of an eye or a counterfeit eye even if it is shot with coaxial incident illumination. The present embodiment utilizes this point of view to discriminate between a living eye and a photograph or a counterfeit eye.

Herein, an average value of luminance values in the pupil region is used for the living eye judgment. When the average value is larger than a predetermined threshold value TH1, it is judged that the retinal reflex is caused, resulting in judgment that the eye included in the image is a living eye.

Figure 3:
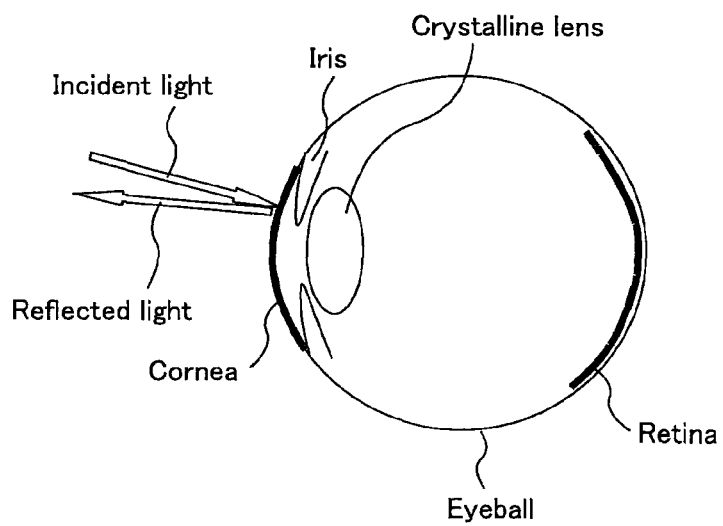
FIG. 3 is a view illustrating a mechanism of a corneal reflex.

Further, for eliminating influence of a corneal reflex within the pupil region, only pixels of which luminance values are smaller than a predetermined threshold value TH2 may be used in calculation of the average value of the luminance values in the pupil region. FIG. 3 shows a mechanism of the corneal reflex. As shown in FIG. 3, light is reflected on a cornea on the surface of the eyeball upon the corneal reflex.

Referring to one of characteristics of the corneal reflex, the luminance is higher than that upon the retinal reflex and is liable to be saturated. Hence, appropriate setting of the threshold value TH2 can eliminate influence of the cornea reflex easily.

Figure 9:
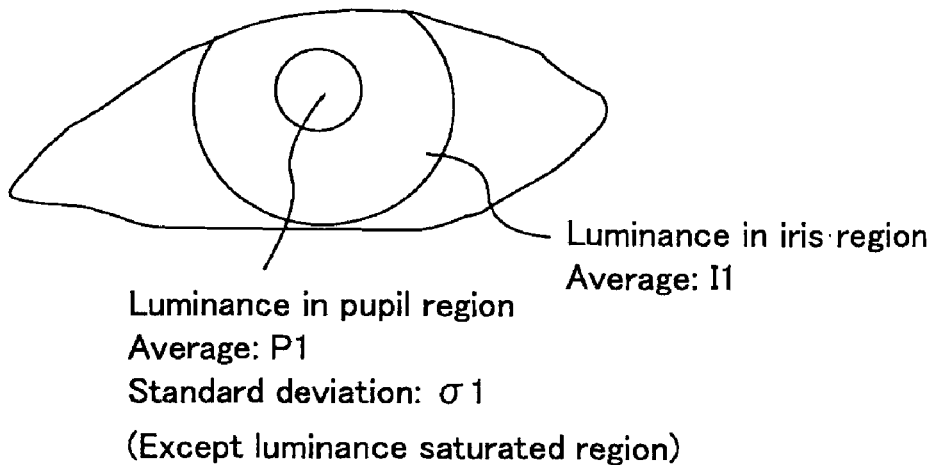
FIG. 9 is a schematic view of an image obtained by shooting a living eye with coaxial incident illumination.
Figure 10:
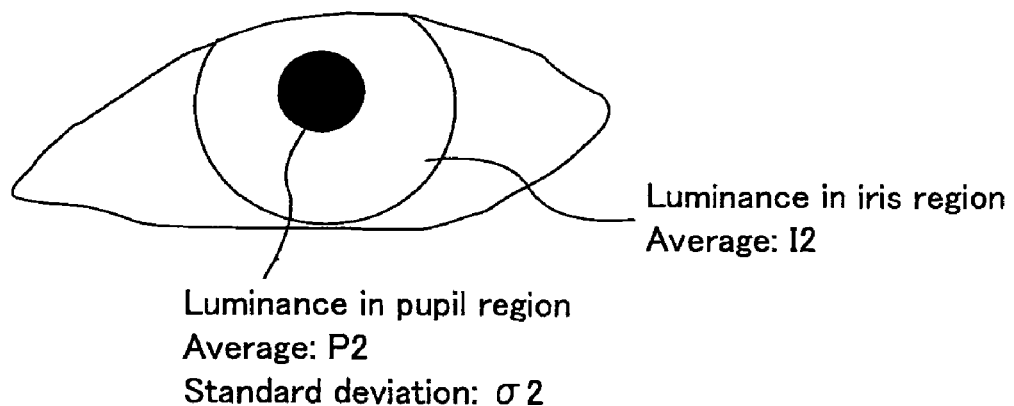
FIG. 10 is a schematic view of an image obtained by shooting a printed output with coaxial incident illumination.

FIG. 9 is a schematic view of an image obtained by shooting a real eye with the use of coaxial incident illumination, and FIG. 10 is a schematic view of a living eye image obtained by shooting a printed image with the use coaxial incident illumination. The retinal reflex is caused in the image including the real eye as shown in FIG. 9, and no retinal reflex is caused in the image obtained by shooting the printed output as shown in FIG. 10. Suppose that the average values of the luminance values in the pupil regions (excluding luminance saturated regions) are P1 in FIG. 9 and P2 in FIG. 10, respectively. Accordingly, setting of the threshold value TH1 in the range of P2<TH1<P1 attains judgment as to whether the eye included in the image is a living eye.

The brightness of images varies, of course, according to the strength of the illumination, the lens aperture, and the black level and gain of the camera, and therefore, the threshold value TH1 may be adjusted according to these values.

As can be understood from FIG. 2(b), the retinal reflex increases the luminance values in the pupil region substantially uniformly. Therefore, a condition as to whether variance or standard deviation of the luminance values in the pupil region is smaller than a predetermined threshold value TH3 or not may be added to conditions for judgment. Suppose that the standard deviation of the luminance values in the pupil region (excluding the luminance saturated region) is σ1 in FIG. 9, the threshold value TH3 may be set in the range of TH3>σ1. The judgment using not only the average value of the luminance values in the pupil region but also the standard deviation attains further accurate living eye judgment.

It is also possible to compare the luminance between in the pupil region and in the iris region of each image. For example, when the luminance in the pupil region is higher than the luminance in the iris region, the image is judged as a living eye image. The image of FIG. 10 is judged as an image including no living eye by utilizing the fact that the luminance value P2 in the pupil region is smaller that the luminance value I2 in the iris region. On the other hand, the image of FIG. 9 is judged as a living eye image by utilizing the fact that the luminance value P1 in the pupil region is larger than the luminance value 11 in the iris region.

Moreover, it is possible to set a condition as to whether a difference in the luminance between in the pupil region and in the iris region is larger than a predetermined threshold value TH4 or not as a condition for living eye judgment. The difference in luminance is expressed as P1-I1 in the image of FIG. 9 and as P2-I1 in the image of FIG. 10. Accordingly, setting of the threshold value TH4 in the range of P2-I2<TH4<P1-I1 attains judgment that the eye included in the image of FIG. 10 is not a living eye.

Furthermore, it is possible to set a condition as to whether a luminance ratio of the pupil region to the iris region is larger than a predetermined threshold value TH5 as a condition for living eye judgment. The luminance ratio is expressed as P1/I1 in the image of FIG. 9 and P2/I2 in the image of FIG. 10. Accordingly, setting of the threshold value TH5 in the range of P2/I2<TH5<P1/I1 attains judgment that the eye included in the image of FIG. 10 is a living eye.

As described above, according to the present embodiment, discrimination between a living eye and a photograph or a counterfeit eye can be performed, using an image obtained by shooting a subject with the illumination coaxial with the optical axis of the camera, based on the luminance in the pupil region. Thus, living eye judgment can be realized by a simple method. Also, false acceptance of one which is not a living eye is prevented and the reliability increased in, for example, personal authentication.

Wherein, the eye of a subject to be shot must be in front of the camera 11 for causing an outstanding retinal reflex. In this connection, a marker for guiding a line of sight may be provided at the center of the visible light cut filter 14 or of a transparent cover provided before the shooting device 10. Further, a visible light illumination for guiding a line of sight may be provided next to the illumination 12 separately. In this case, the visible brightness of the visible light illumination is set to the lowest level so that a subject to be shot feels no glare.

Wherein, FIG. 4 shows the flow of the living eye judgment after the iris authentication and FIG. 7 shows the flow of the iris authentication after the living eye judgment, but the iris authentication and the living eye judgment are not necessarily performed in series. For example, they may be performed in parallel with the use of two processors of, for example, the iris authentication section 16 and the living eye judgment section 17.

<"Coaxial">

In the present embodiment, a subject is illuminated coaxially with the optical axis of the camera. The term "coaxial" in this embodiment does not strictly require the coaxial state and means a "substantially coaxial state" to the extent that attains retinal reflex shooting. Namely, the term "coaxial" in the present invention includes not only the strict coaxial state but also the substantially coaxial state within the range where the retinal reflex can be shot.

Figure 11:
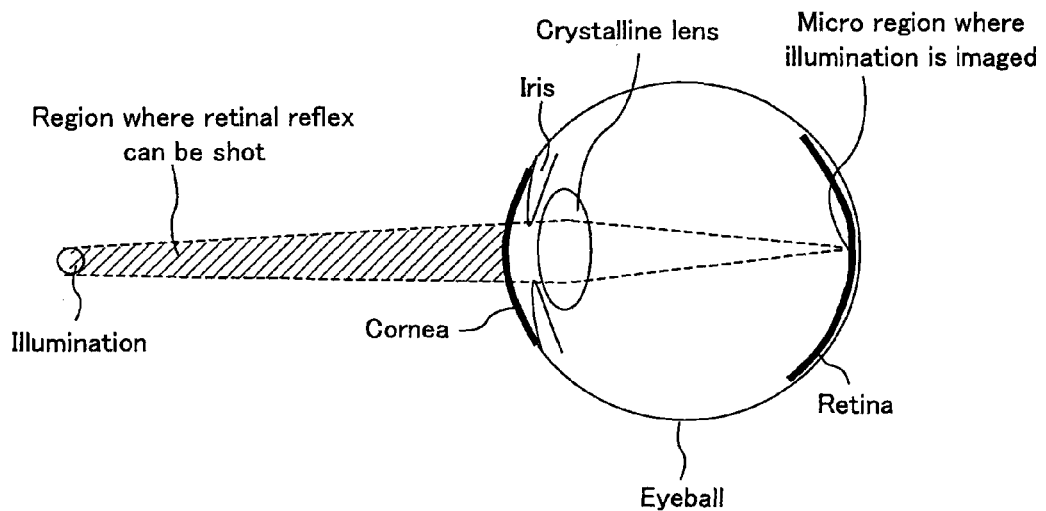
FIG. 11 is a view illustrating the range where retinal reflex can be shot.
Figure 12:
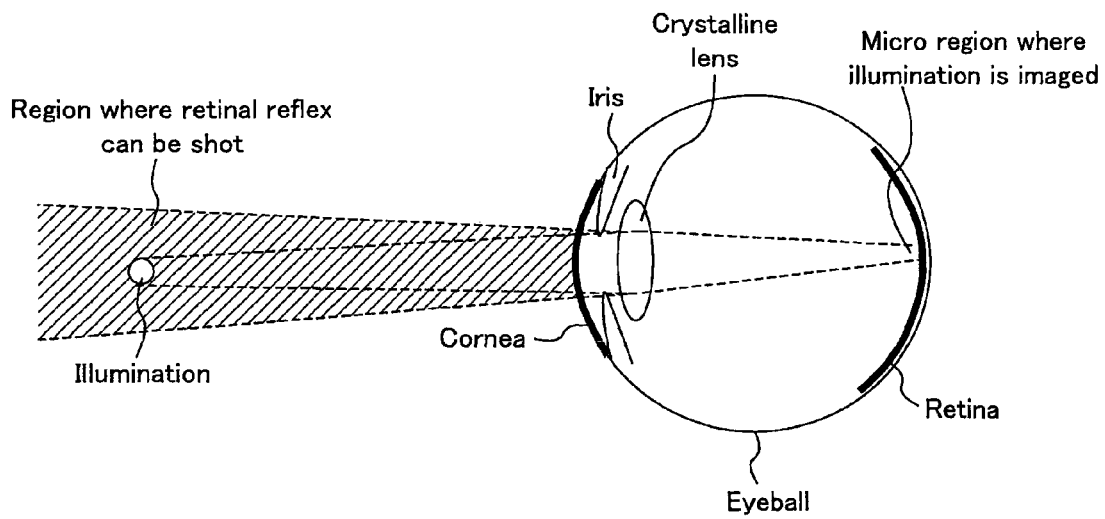
FIG. 12 is a view illustrating the range where retinal reflex can be shot.

With reference to FIG. 11 and FIG. 12, the range where the retinal reflex can be shot will be explained. Incident light of illumination is refracted through a crystalline lens corresponding to a lens to form an image. The illumination light imaged on the retina is refracted through the crystalline lens to get out of the eyeball. When a living eye comes into focus on the illumination and there is no aberration by the crystalline lens corresponding to the lens, the illumination light imaged on the retina is condensed again at the position of the illumination as shown in FIG. 11. Thus, the arrangement of the camera in the hatched region in FIG. 11 enables retinal reflex shooting.

On the other hand, in either case where a living eye is out of focus on the illumination or there is aberration by the crystalline lens, the region where the retinal reflex can be shot becomes wider as shown in FIG. 12.

Accordingly, the case where the optical axis of the camera is included in the hatched region in FIG. 11 or FIG. 12 is defined as the substantially coaxial state to the extent that enables the retinal reflex shooting, and is included in the "coaxial state" in the present invention.

For information, the retinal reflex is caused even if the illumination is displaced from the optical axis of the camera. As an example of the retinal reflex in such a case, a red-eye phenomenon by a flash of a camera is raised. In ordinary cameras, the lens and the flash are arranged at positions different from each other, of which distance is shorter than a shooting distance. Therefore, the red-eye as a retina reflex is shot though the flash is not perfectly coaxial.

<Other Constitutions of Shooting Device>

In the present embodiment, the half mirror 13 is provided for setting the illumination 12 coaxially with the optical axis of the camera 11. However, inverse arrangement of the illumination 12 and the camera 11 with the half mirror 13 interposed may be possible. In this case, light of the illumination 12 passes through the half mirror 13 to illuminate the eye EY, while the camera 11 captures an image reflected on the half mirror 13.

Figure 13:
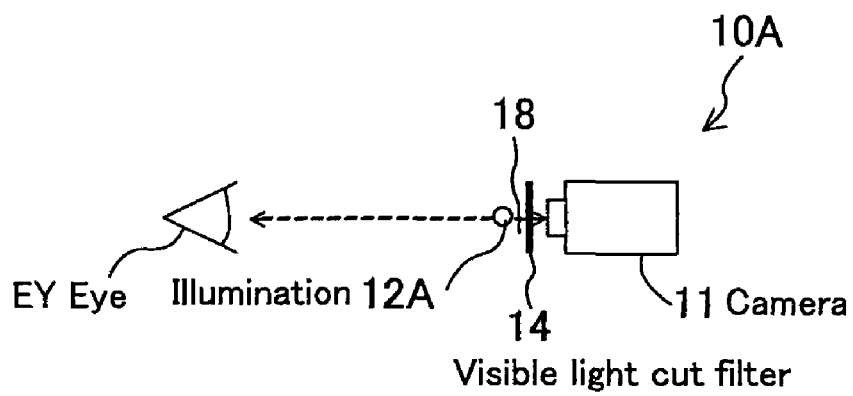
FIG. 13 shows another example of the constitution of a shooting device according to each embodiment of the present invention.
Figure 14:
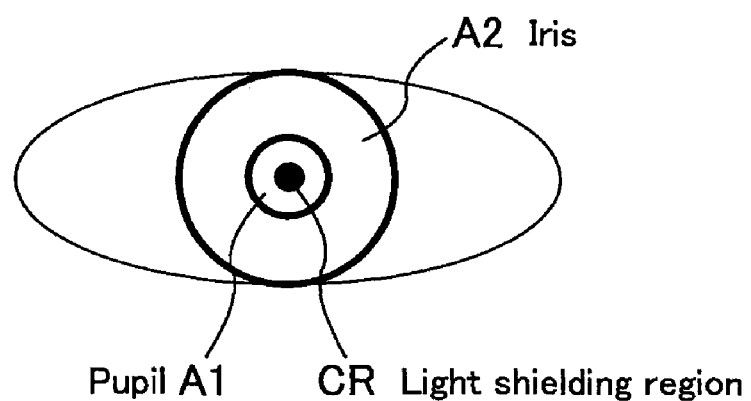
FIG. 14 is a schematic view of an image obtained by the shooting device of FIG. 13.

Further, the constitution for the illumination coaxial with the optical axis of the camera can be realized with no use of such a half mirror. For example, in a shooting device 10A in FIG. 13, an illumination 12A as illumination means is arranged on the optical axis and before the camera 11. Wherein, this constitution necessitates light shielding means 18 between the illumination 12A and the camera 11 for preventing light of the illumination 12A from being made incident directly into the camera 11. As a matter of course, a subject cannot be shot through the region of the light shielding means 18, so that the image obtained by the shooting device 10A of FIG. 13 shall include a light shielding region CR in the pupil region A1. However, this involves no problem because only an image of the iris region A2 suffices for the iris authentication.

Figure 15:
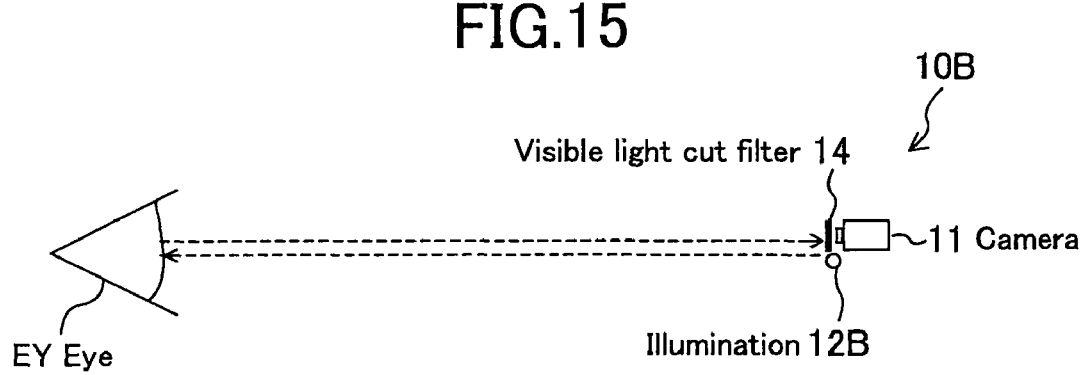
FIG. 15 shows another example of the constitution of a shooting device according to each embodiment of the present invention.
Figure 16:
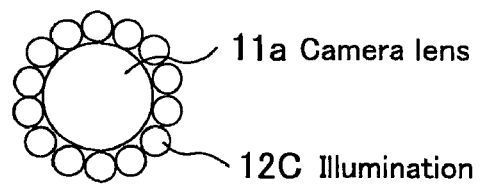
FIG. 16 shows a modified example of illumination layout in FIG. 5.

Further, in a shooting deice 10B of FIG. 15, an illumination 12B as illumination means is displaced slightly from the optical axis of the camera 11. Wherein, the camera 11 is positioned so as to be included in the region where the retinal reflex can be shot as shown in FIG. 12. In other words, the eye EY of a person to be shot is illuminated "coaxially" with the optical axis of the camera 11. In addition, as a modification of FIG. 15, a plurality of illuminations 12c as illumination means may be arranged around a camera lens 11a as shown in FIG. 16.

SECOND EMBODIMENT

An iris authentication method according to the second embodiment of the present invention is the same in the basic processing flow as in the first embodiment. It is the difference that living eye judgment is performed in such a manner that a second image is obtained by shooting a subject with illumination of which optical axis is different from the optical axis of a camera separately from a first image obtained by shooting the subject with illumination coaxial with the optical axis of the camera and the first and second images are used.

Figure 17:
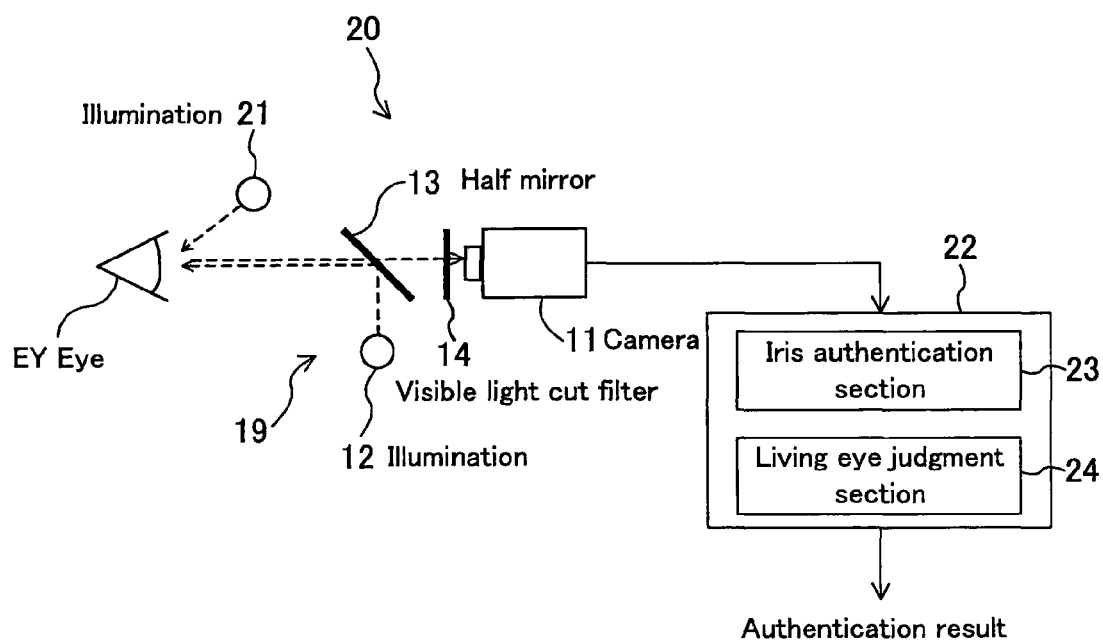
FIG. 17 shows one example of the constitution of an iris authentication device including a living eye judging device according to the second embodiment of the present invention.

FIG. 17 shows one example of the constitution of an iris authentication device according to the present embodiment, wherein the same reference numerals as in FIG. 5 are assigned to the common constitutional elements in FIG. 5. Different from the shooting device 10 in FIG. 5, a shooting device 20 in FIG. 17 is provided with an illumination 21 in addition to the illumination 12. The illumination 21 illuminates the eye EY of a person to be shot directly on an optical axis different from the optical axis of the camera 11 (i.e., non-coaxial illumination, instead of coaxial incident illumination). The illumination 12 and the half mirror 13 compose first illumination means 19, while the illumination 21 composes second illumination means. Also, an image processing section 22 is provided with an iris authentication section 23 and a living eye judgment section 24 for executing iris authentication including living eye judgment on an eye image obtained by the shooting device 20. The shooting device 20 and the living eye judgment section 24 compose a living eye judgment device.

The processing in the present embodiment will be described here with reference to the flow of FIG. 4. It is, of course, possible to perform the living eye judgment before the iris authentication as shown in FIG. 7, or to perform the iris authentication and the living eye judgment in parallel.

First, in the step S11, the shooting device 20 shoots an iris image. Herein, shooting is performed for the case with illumination by the illumination 12 only and for the case with illumination by the illumination 21 only. An image obtained with the use of the illumination by only the illumination 12, that is, an image obtained with coaxial incident illumination is used as a first image, and an image obtained with illumination by only the illumination 21, that is, an image obtained without coaxial incident illumination is used as a second image.

Next, in the step S12, the iris authentication is performed using the images obtained in the step S11. The iris authentication section 23 executes this processing. In the iris authentication, at least one of the first and second images is used. Herein, the second image is used for the authentication. Of course, the first image may be used for the authentication. Also, it is possible that the authentication is performed using both the first and second images and, for example, final authentication success is attained when either one is judged as authentication success or final authentication success is attained when both of them are judged as authentication success. The authentication policy may be determined according to the security level. The method of the iris authentication is as described as in the first embodiment.

Then, in the step S13, whether the authentication has been succeeded or not is checked. When the authentication has been succeeded (Yes), the routine proceeds to the step S14, but otherwise (No), the person to be authenticated is rejected as a non-registrant and the processing terminates.

In the step S14, the living eye judgment is performed. The details are described later. When the judgment results in that the eye included in the image is not a living eye (No in S15), the person to be authenticated is rejected and the processing terminates. On the other hand, when the judgment results in that the eye included in the image is a living eye (Yes in S15), the processing terminates as authentication success.

Herein, the living eye judgment in the step S14 will be described in detail along the flow of FIG. 8. The processing herein corresponds to the living eye judging method according to the present embodiment.

First, in the step S31, pupil regions are determined for the first and second images. Herein, the position of the pupil in the second image has been obtained already in the step S12, and therefore, determination is made only for the pupil region in the first image. Wherein, in the case where a shooting interval between the fist and second images is short, for example, in the case where they are shot serially by a camera at 30 frames/s, it is considered that the pupil region scarcely changes between the first and second images. Therefore, the pupil position in the second image may be employed as the pupil position in the first image. Further, in the case where the living eye judgment S22 is performed before the iris authentication S24 as in the flow of FIG. 7, the pupil regions are determined in this time. Any optional methods may be used for determining the pupil regions and, for example, the method disclosed in Patent Document 1 may be employed.

Next, in the step S32, whether the eye included in the image is a living eye or not is judged based on luminance in the pupil regions of the first and second images. In an image including a living eye, the luminance in the pupil region as a whole is high because of the retinal reflex in the case using coaxial incident illumination and is low in the case using non-coaxial incident illumination. Discrimination between a living eye and a photograph or a counterfeit eye is performed by utilizing this point of view in the present embodiment.

Herein, an average value of luminance values in the pupil region is used for the living eye judgment. Suppose that the average values of the luminance values in the pupil regions of the first and second images are Pa and Pb, respectively. When a luminance difference (Pa-Pb) is larger than the predetermined threshold value TH1, it is judged that retinal reflex is caused and is judged that the eye included in the image is a living eye.

Figure 18:
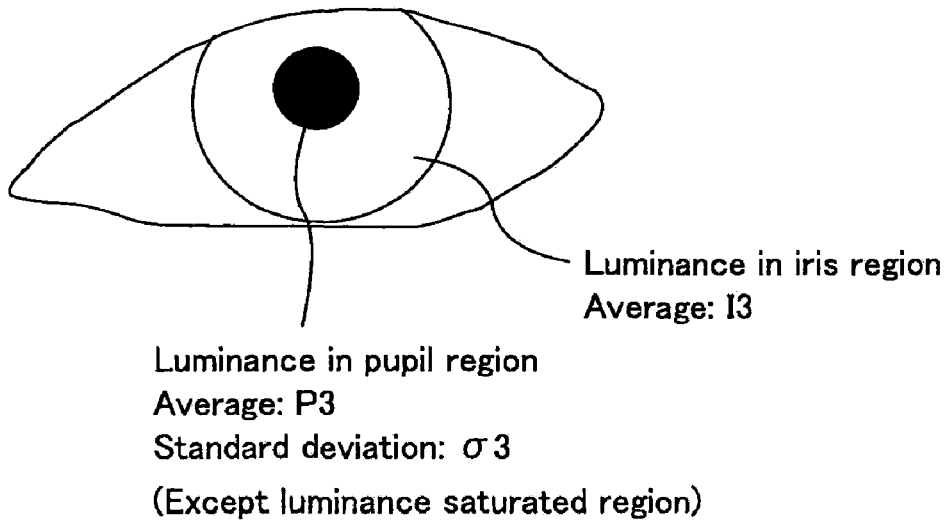
FIG. 18 is a schematic view of an image obtained by shooting a living eye with non-coaxial illumination.
Figure 19:
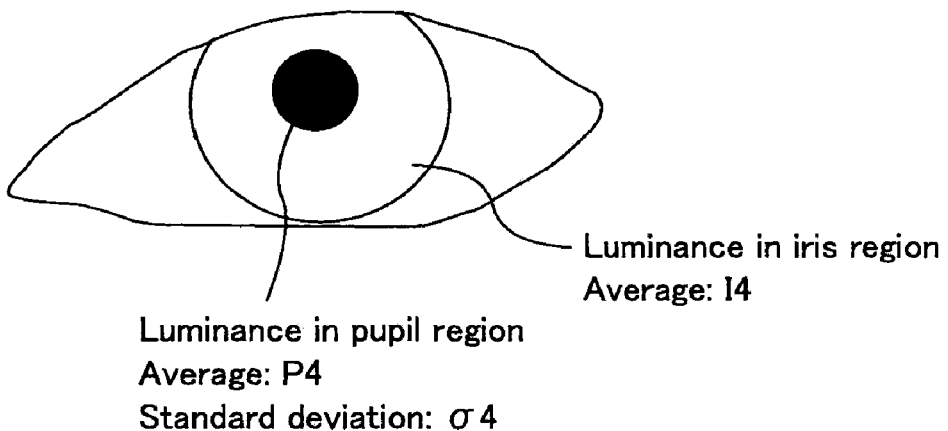
FIG. 19 is a schematic view of an image obtained by shooting a printed output with non-coaxial illumination.

FIG. 18 and FIG. 19 are examples of the second image obtained with non-coaxial illumination, wherein FIG. 18 is an image including a real eye and FIG. 19 is an image obtained by shooting a printed output. Further, suppose that the images of FIG. 9 and FIG. 10 are obtained as the first images obtained by shooting with the coaxial incident illumination, the luminance difference (Pa-Pb) is P1-P3 in the image of the real eye (FIG. 9 and FIG. 18) and is P2-P4 in the image of the printed output (FIG. 10 and FIG. 19). Accordingly, setting of the threshold value TH1 in the range of P2-P4<TH1<P1-P3 attains discrimination between a living eye and an eye that is not a living eye.

Further, it is possible to judge the eye included in the image as a living eye when the luminance average value Pa in the pupil region of the first image is larger than the predetermined threshold value TH2 and the luminance average value Pb in the pupil region of the second image is smaller than the predetermined threshold value TH3.

Or, a difference in the luminance between the pupil region and the iris region may be used. Suppose that the luminance average value in the iris image of the first image and the luminance average value in the iris region of the second image are Ia and Ib, respectively. For example, when an absolute value of a difference between the luminance difference in the first image, that is, a first difference (Pa-Ia) and the luminance difference in the second image, that is, a second difference (Pb-Ib) is larger than the threshold value TH4, the eye included in the image is judged as a living eye. In the previous image examples, the luminance difference (Pa-Ia) in the first image (FIG. 9), the luminance difference (Pb-Ib) in the second image (FIG. 18) and the absolute value of the difference therebetween are P1-I1, P3-I3 and |(P1-I1)-(P3-I3)|, respectively, for a real eye. On the other hand, the luminance difference (Pa-Ia) in the first image (FIG. 10), the luminance difference (Pb-Ib) in the second image (FIG. 19) and the absolute value of the difference therebetween are P2-I2, P4-I4 and |(P2-I2)-(P4-I4)|, respectively, for a printed output. Accordingly, setting of the threshold value TH4 in the range of |(P2-I2)-(P4-I4)|<TH4<|(P1-I1)-(P3-I3)| attains judgment as to whether the eye included in the image is a living eye or not. This is equivalent to the use of an absolute value of the difference between a calculated difference in luminance in the pupil region between the first and second images and a calculated difference in luminance in the iris region between the first and second images. Namely, |(Pa-Ia)-(Pb-Ib)| is |(Pa-Pb)-(Ia-Ib)|.

Further, it is possible to judge the eye included in the image as a living eye when the luminance difference (Pa-Ia) in the first image is larger than a predetermined threshold value TH6 and the luminance difference (Pb-Ib) in the second image is smaller than the predetermined threshold value TH5.

Or, a luminance ratio of the pupil region to the iris region may be used. For example, the eye included in the image is judged as a living eye when the luminance ratio in the first image, that is, a first ratio Pa/Ia to the luminance ratio in the second image, that is, a second ratio Pb/Ib is larger than a threshold value TH7. In the previous image examples, the luminance ratio Pa/Ia in the first image (FIG. 9), the luminance ratio Pb/Ib in the second image (FIG. 18) and the ratio thereof are P1/I1, P3/I3 and P1/I1/(P3/I3), respectively, for a real eye. On the other hand, the luminance ratio Pa/Ia in the first image (FIG. 10), the luminance ratio Pb/Ib in the second image (FIG. 19) and the ratio thereof are P2/I2, P4/I4 and P2/I2/(P4/I4), respectively, for a printed output. Accordingly, setting of the threshold value TH7 in the range of P2/I2/(P4/I4)<TH7<P1/I1/(P3/I3) attains judgment as to whether the eye included in the image is a living eye or not. This is equivalent to the use of the ratios of a calculated luminance ratio in the pupil regions of the first and second images and a calculated luminance ratio in the iris region of the first and second images. Namely, (Pa/Ia)/(Pb/Ib) is (Pa/Pb)/(Ia/Ib).

Moreover, it is possible to judge the eye included in the image as a living eye when the luminance ratio Pa/Ia in the first image is larger than a predetermined threshold value TH9 and the luminance ratio Pb/Ib in the second image is smaller than a predetermined threshold value TH8.

In addition, in order to avoid influence of the corneal reflex within the pupil region, only pixels of which luminance values are smaller than a predetermined threshold value TH10 may be used in calculation of the average value of the luminance values in the pupil region. Further, a condition as to whether the variance or standard deviation of the luminance values in the pupil region is smaller than a predetermined threshold value TH11 or not may be added to the conditions for living eye judgment, utilizing the fact that the luminance values in the pupil region are almost uniformly large upon the retinal reflex.

As described above, according to the present embodiment, discrimination between a living eye and a photograph or a counterfeit eye is attained by using an image obtained by shooting a subject with the illumination coaxially with the optical axis of a camera and an image obtained by shooting the subject with the illumination of which optical axis is different from the optical axis of the camera, based on the luminance in the pupil regions of both the images. Hence, highly accurate living eye judgment is realized by a simple method. False authentication of one that is not a living eye can be prevented and the reliability can be enhanced in, for example, personal authentication.

It is noted that only the illumination 12 is lighted during shooting of the first image and only the illumination 21 is lighted during shooting of the second image in the present embodiment, but the illumination 12 and the illumination 21 may be lighted concurrently for shooting the first image. In this case, if the luminance in the iris region is secured by the illumination 21 and the illumination 12 is set to a minimum light level for causing the retinal reflex, a burden on living eyes by light illumination to the vicinity of the central region of the retinas can be reduced.

It is also noted that, for illumination non-coaxial with the camera, the optical axis is displaced to such an extent that no retinal reflex is caused.

THIRD EMBODIMENT

The basic processing flow of an iris authentication method according to the third embodiment of the present invention is the same as that in the first embodiment. It is the difference therefrom that a plurality of images are obtained in shooting of a subject with the illumination coaxial with the optical axis of the camera and living eye judgment is performed using the plural images.

The device in FIG. 5 is used as an iris authentication device according to the present embodiment, likewise the first embodiment. The constitutional elements in FIG. 5 are the same as those in the first embodiment, and the description thereof is omitted.

The processing in the present embodiment will be described with reference to the flow of FIG. 4. Of course, the living eye judgment may be performed before the iris authentication as shown in FIG. 7, or may be performed in parallel to the iris authentication.

First, in the step S11, the shooting device 10 shoots a plurality of iris images. Herein, iris images are shot at a shooting speed of 30 frames per second, and the illumination 12 is lighted in synchronization with exposure of the camera 11.

Next, in the step S12, the iris authentication is performed using the plural images obtained in the step S11. The iris authentication section 16 executes this processing.

Herein, image quality is judged separately and one of images of which evaluation value by the image quality judgment is the maximum is used for the iris authentication. A focus value, opening of an eye lid and the like may be used as the image quality. Of course, any image out of the plural shot images may be used for the authentication. Also, it is possible that the authentication is performed using all the iris images and, for example, the eye included in the image is judged as final authentication success upon authentication success in any one of the images or it is judged as final authentication success upon authentication success of a predetermined rate of the iris images. The authentication policy may be determined according to the security level. The iris authentication method is as described in the first embodiment.

Then, in the step S13, whether the authentication has succeeded or not is checked. If the authentication has succeeded (Yes), the routine proceeds to the step S14. Otherwise (No), the person to be authenticated is rejected as a non-registrant and the processing terminates.

In the step S14, living eye judgment is performed. The living eye judgment section 17 executes this processing, which will be described later. If the judgment results in that the eye included in the image is not a living eye (No in S15), the person to be authenticated is rejected and the processing terminates. On the other hand, if the judgment results in that the eye included in the image is a living eye (Yes in S15), the processing terminates as authentication success.

Figure 8:
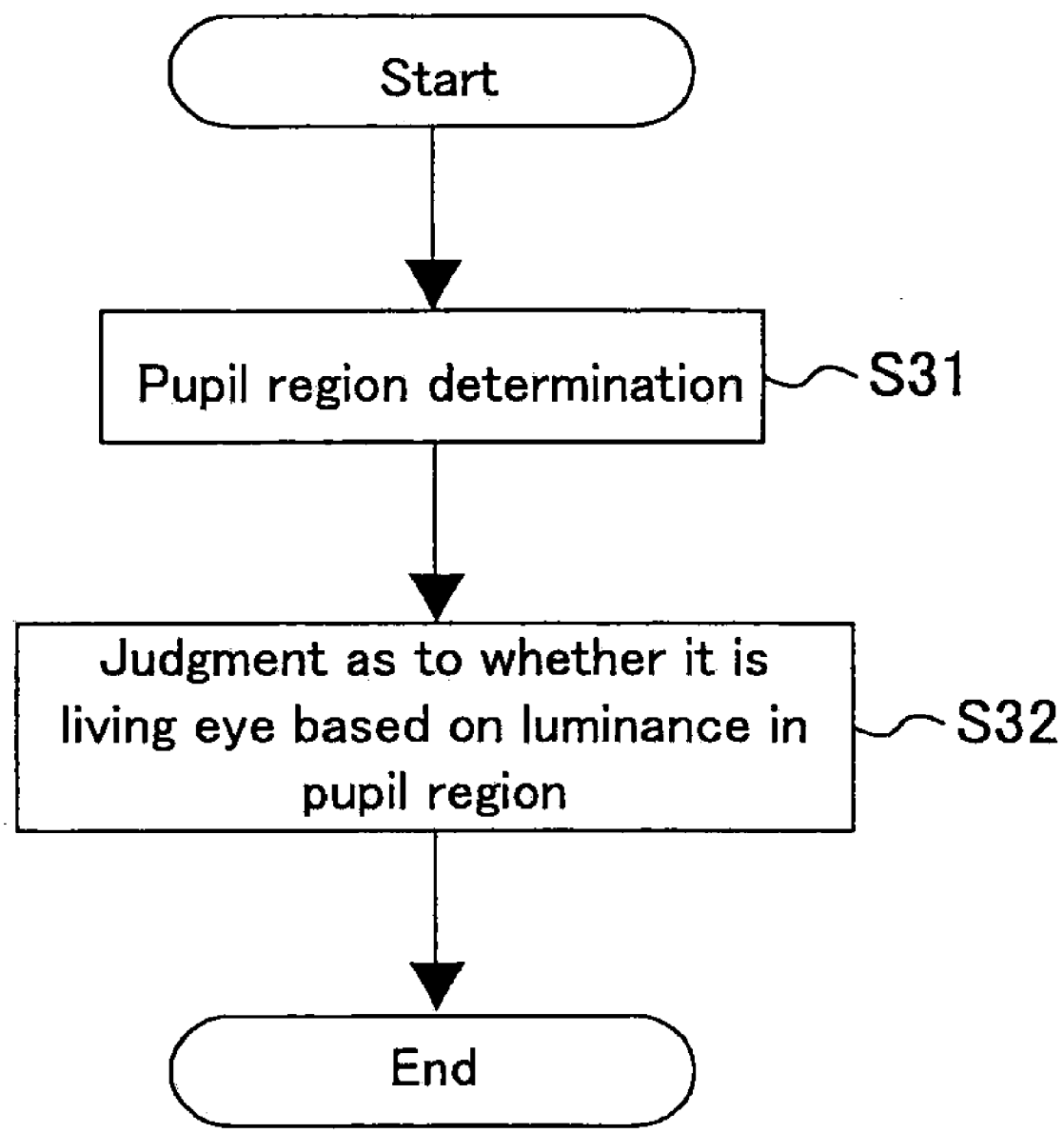
FIG. 8 is a flowchart showing a living eye judging method.

Herein, the living eye judgment in the step S14 in the present embodiment will be descried in detail along the flow of FIG. 8. The processing herein corresponds to the living eye judgment method according to the present invention.

First, in the step S31, the pupil regions are determined for the plural shot iris images. In the case of serial shooting at a shooting speed of 30 frame per second, it can be considered that the pupil regions scarcely change their positions among the plural iris images. Therefore, a search region for the pupil region is set slightly large only for the first image and only the vicinity thereof is searched for the second and following images, using the iris region of the previous frame as an initial value for search. Thus, the calculation amount is reduced. Any optional methods may be employed as the determination of the pupil region. For example, the method disclosed in Patent Document 1 may be employed.

Next, in the step S32, whether the eyes included in the images are a living eye or not is judged based on the luminance in the pupil regions of the plural images. It should be noted that a pupil of a living eye repeats minute contraction and dilator even at a constant brightness therearound. In short, generally called hippus is caused. In the present embodiment, time variation in a predetermined index based on the luminance in the pupil region is obtained from plural images shot with coaxial illumination which might cause the retinal reflex if it is a living eye. Then, the presence or absence of the hippus is detected from the time variation of the index to judge whether the eye included in the image is a living eye.

It is noted that the degree of the hippus, namely, the degree of contraction and dilator of the pupil is measured directly from the time variation of the pupil diameter. However, actual experiments by the present inventors reveals difficulty in accurate measurement of the variation in pupil diameter in ordinary iris authentication because of the following reason.

Namely, iris images used for iris authentication are shot at resolution that allows the diameter of an iris to have approximately 200 pixels according to specification of cameras in general. Also, the opening of the pupil, which includes difference to some degree among persons, is approximately 0.40 in a ratio of the pupil diameter to the iris diameter under circumference of normal brightness and the pupil diameter at that time has approximately 80 pixels. Further, according to the inventors' experiments, the range of the pupil diameter varied by hippus under such conditions is 3.7 pixels in standard deviation (an average value of four subjects). It is inferred that accurate measurement of the periodic variation within about 3 to 4 pixels in standard deviation is considerably difficult because of the presence of error in detection the pupil region and the like. Therefore, it is considered difficult to detect the variation in pupil diameter to sufficiently accurate degree under general shooting circumstance in performing iris authentication.

Under the above circumstances, the presence or absence of minute variation in pupil diameter is judged based on the time variation of an index for luminance in the pupil region under the coaxial illumination. Upon the retinal reflex by coaxial illumination, the pupil region becomes bright as the quantity of light passing through the pupil and reaching the retina is large, in other words, as the pupil diameter becomes large. Therefore, the use of the luminance in the pupil region (i.e., retinal reflex) or the time variation of the index for the luminance attains judgment as to the presence or absence of contraction and dilator of the pupil.

Various indexes can be considered as the predetermined index for the luminance. For example, an average value of luminance values of pixels included in the pupil region may be used as the predetermined index. In this case, an average value of luminance values in a region except a corneal reflex region upon specular reflection (corneal reflex) caused in the pupil region is calculated. The luminance value becomes remarkably large in general in the corneal reflex region. Therefore, setting of an appropriate threshold value for the luminance leads to specification of the region.

It is also possible to use the luminance ratio of the pupil region to the iris region as the predetermined index. The use thereof provides robustness for change in circumstances.

Referring to the change in circumstances, it is considered, for example, that a distance between the coaxial illumination and a subject during shooting of a plurality of images is changed. In a fixed shooting device such as an entrance/exit management device, movement of the head of a subject changes the distance between the coaxial illumination and the subject. In a handy shooting device, also, movement of the hand holding the device and movement of the head of a subject change the distance between the coaxial illumination and the subject. In the case where the illumination emits incompletely parallel light, variation in distance from the illumination changes the luminance of the pupil region accordingly. As a result, accurate measurement of hippus may not be necessarily possible based on the luminance in the pupil region only.

On the other hand, while being constant under constant illumination, the luminance in the iris region varies according to change in distance between the coaxial illumination and a subject likewise the luminance in the pupil region. Therefore, the use of the luminance ratio of the pupil region to the iris region attains accurate measurement of luminance variation by contraction and dilator of the pupil, with influence of the variation in circumstances eliminated.

Furthermore, a total sum of the luminance values of the pixels in the pupil region may be used as the predetermined index. In detail, during dilator of the pupil, the luminance in the pupil region on retinal reflex increases and the aria of the pupil region increases. On the other hand, during contraction of the pupil, the luminance in the pupil region decreases and the area of the pupil also decreases. Therefore, the use of the total sum of the luminance values in the pupil region as the index highlights the time variation of the index by hippus, compared with the case using the average value of the luminance values. Hence, S/N in measured noise can be increased and accuracy in measurement can be enhanced.

Moreover, it is possible to use a value normalized by the area of the iris region as the total sum of the luminance values of pixels in the pupil region. For example, variation in the distance between the illumination and a subject changes resolution in addition to the change in the luminance in the pupil region. Under the circumstances, the total sum of the luminance values in the pupil region is normalized by the luminance value (e.g., an average value) in the iris region for eliminating influence of variation in luminance, and then, is further normalized by the area of the iris region. In so doing, influence of variation in resolution can be also eliminated. An area of a circle ($\pi r^2$ when the iris diameter includes r pixels) representing an iris perimeter (see FIG. 6) may be used as the area of the iris region, for example. Or, an area of an iris region which is exposed actually may be used. It is noted that normalization using the total sum of the luminance values of pixels in the iris region, instead of normalization by the luminance values and area of the iris region, can attain the same effect. Also, normalization only by the area without the processing for normalization by the luminance values in the iris region may be possible.

Figure 20:
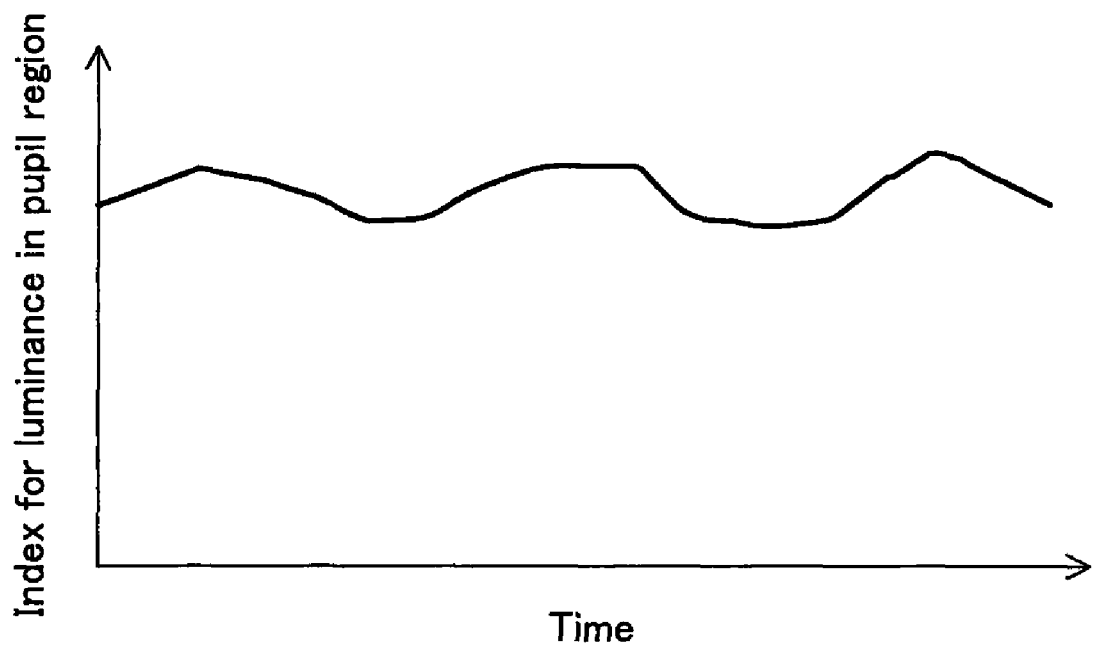
FIG. 20 is a schematic graph showing time variation in a predetermined index of luminance in a pupil region according to the third embodiment of the present invention.

FIG. 20 is a schematic view showing the thus obtained time variation of the index for the luminance value of the pupil region. Though the range of variation along the axis of ordinates is different according to the kind of the index, periodic variation caused due to hippus as shown in FIG. 20 can be obtained for a living eye.

Figure 21:
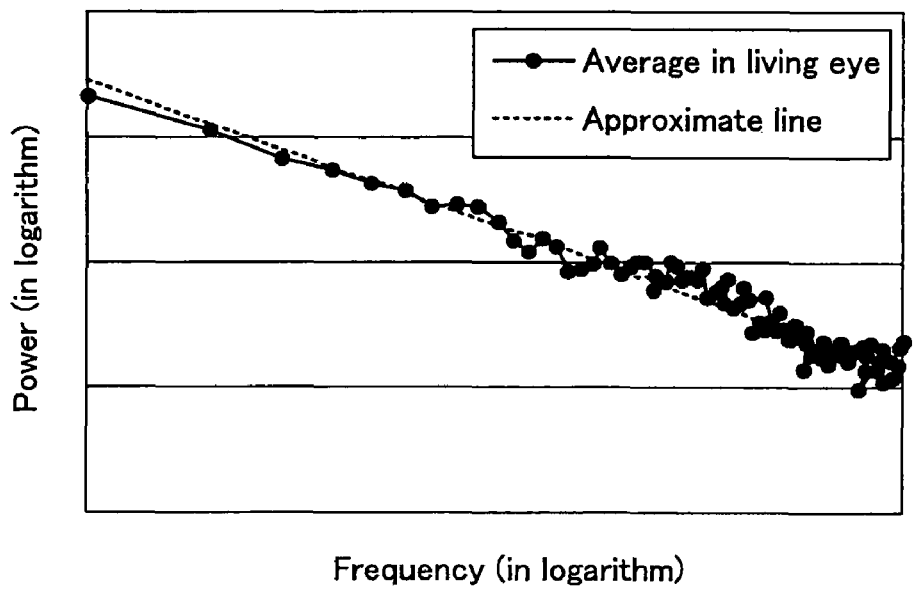
FIG. 21 shows an example of a frequency characteristic obtained from the index time variation in FIG. 20.

Subsequently, whether the eye included in the image is a living eye or not is judged from the index time variation as in FIG. 20. Herein, Fourier transform is applied to the index time variation as in FIG. 20 to perform judgment using a frequency characteristic. FIG. 21 is a graph showing the relationship between the frequency obtained from the index time variation and power. FIG. 21 uses the luminance sum in the pupil region as the predetermined index and plots averages of frequency characteristics in 40 sequences (4 eyes×10 sequences). The axis of abscissas indicates the frequency and the axis of ordinates indicates the power, both of which are expressed in logarithms. FIG. 21 also shows a broken line as linear approximation of the plots. FIG. 21 indicates substantially linear decrease of the logarithmic power with respect to the logarithmic frequency, namely, it clarifies 1/f characteristic imparted. Accordingly, the living eye judgment can be performed based on whether the frequency characteristics of the sequence shots at authentication fall in the 1/f characteristic.

It is noted that the variation in pupil diameter can be accurately obtained in the case with sufficient shooting resolution or the case where the variation in pupil diameter can be magnified (for example, the case where visible light illumination in the shooting circumstance is changed, wherein illumination strength of near-infrared light for causing the retinal reflex is constant). In this case, the living eye judgment may be performed based on the frequency characteristic of the time variation in pupil diameter.

Figure 22:
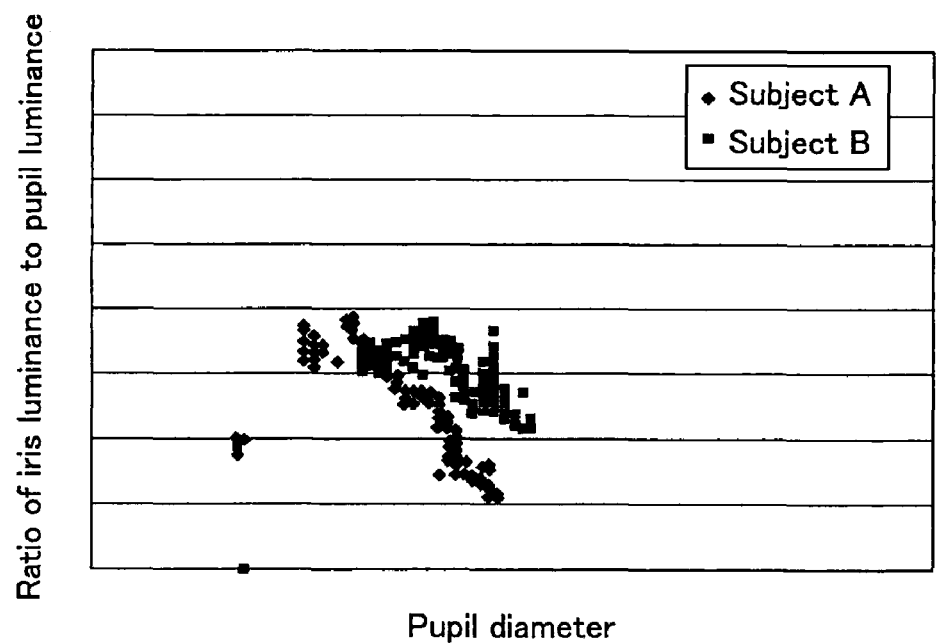
FIG. 22 is a graph showing the relationship between a pupil diameter and a ratio of iris luminance to pupil luminance.

Furthermore, it is possible to use the pupil diameter and the luminance of the pupil region. For example, the living eye judgment may be performed by utilizing the fact that the correlation is present or not between the pupil diameter and the luminance of the pupil region. FIG. 22 is a graph showing the relationship between the pupil diameter and the ratio of the iris luminance to the pupil luminance. FIG. 22 expresses data of two persons obtained by shooting 30 frames of iris images per second while changing the strength of the visible light in the shooting circumstance. As can be understood from FIG. 22, the pupil luminance is increased as the pupil diameter increases, with a result of decrease in the ratio of the iris luminance to the pupil luminance. The living eye judgment may be performed based on the fact that such correlation is present or not.

As described above, in the present embodiment, the time variation of a predetermined index for the luminance in the pupil region is obtained from a plurality of images of a subject shot sequentially in time with the illumination coaxial with the optical axis of the camera. Then, discrimination between a living eye and a photograph or a counterfeit eye is performed based on the index time variation. Thus, highly accurate living eye judgment can be realized by a simple method. For example, false authentication of one that is not a living eye can be prevented and the reliability is enhanced, for example, in personal authentication.

Wherein, the above embodiment refers to an example using LEDs as the illumination. LEDs, which has advantages of low power consumption and long lifetime, are light sources of which utilization is being promoted. Wherein, the safety regulation on LEDs is established as a light source following lasers in International Standard IEC60825-1 (JIS C6802). As a matter of course, the safety regulation must be satisfied for commercialization. However, even the LEDs used for the coaxial incident illumination in the living eye judgment, which satisfy the safety regulation, may results in a burden on a person whose eyes are sensitive or tired.

In preparation for such cases, the illumination preferably emits light only during exposure of the camera (e.g., 16 ms or 33 ms). Or, the number of times of the living eye judgment may be limited. For example, the number of authentication per day is counted for each person, and the living eye judgment is prohibited when the number of authentication exceeds the upper limit. Or, another living eye judgment may be performed which uses no coaxial incident illumination.

It is noted that the living eye judgment is performed in combination with the iris authentication in each of the above embodiments but may be used for other purposes. Also, the living eye judgment is performed on near-infrared images in each of the above embodiments but the living eye judgment method according to the present invention is not limited to images shot under near-infrared light illumination and is, of course, applicable to images shot under visible light illumination. In this case, the visible light cut filter 14 is not used. The images for the iris authentication may be shot separately, for example.

In addition, the living eye judgment is executed by the image processing section associated with the shooting device in each of the above embodiments, but the present invention is not limited to such a constitution. For example, it is possible that an eye image is shot by a portable terminal in which the shooting device as shown in FIG. 5 is incorporated, the shot image is sent to a server through a network, and then, the living eye judgment is performed in the server upon receipt of an image. Namely, the constitution, in which an image of an eye shot with coaxial incident illumination only is obtained or an image of an eye shot with non-coaxial incident illumination is also obtained in addition, and then, the processing for judging whether the eye included in each image is a living eye is executed is included in the present invention.

INDUSTRIAL APPLICABILITY

The present invention attains easy judgment as to whether an eye included in an image is a living eye or not based on the luminance in the pupil region of the image, and therefore, unfair pretending using a photograph or a counterfeit eye can be precluded by a simple constitution in, for example, personal authentication using an iris image.

The invention claimed is:

1. A living eye judging method comprising:
   a first step of obtaining an image captured by shooting a subject with illumination coaxial with an optical axis of a camera; and
   a second step of judging whether an eye included in the image is a living eye or not, utilizing that retinal reflex is caused by coaxial incident illumination if the eye is a living eye, based on luminance in a pupil region of the eye in the image.

2. The method of claim 1,
   wherein in the first step, a plurality of images sequential in time are obtained, and
   in the second step, whether the eye is a living eye or not is judged based on time variation in a predetermined index for luminance in the pupil region obtained from the plurality of images.

3. The method of claim 2,
   wherein the predetermined index is an average value of luminance in the pupil region.

4. The method of claim 2,
   wherein the predetermined index is a ratio of luminance of the pupil region to the iris region.

5. The method of claim 2,
   wherein the predetermined index is a total sum of luminance values of each pixel in the pupil region.

6. The method of claim 5,
   wherein the total sum of the luminance values is normalized by an area of the iris region.

7. A living eye judging device comprising:
   a camera for shooting a subject;
   an illumination section for illuminating the subject coaxially with an optical axis of the camera; and
   a living eye judgment section that receives an image captured by the camera with illumination by the illumination section and performs judgment as to whether an eye included in the image is a living eye or not, utilizing that retinal reflex is caused by coaxial incident illumination if the eye is a living eye, based on luminance in a pupil region of the eye in the image.

* * * * *

UNITED STATES PATENT AND TRADEMARK OFFICE
CERTIFICATE OF CORRECTION

| | | |
|---|---|---|
| PATENT NO. | : 7,801,336 B2 | Page 1 of 1 |
| APPLICATION NO. | : 12/390705 | |
| DATED | : September 21, 2010 | |
| INVENTOR(S) | : Kenji Kondo et al. | |

It is certified that error appears in the above-identified patent and that said Letters Patent is hereby corrected as shown below:

On the title page, under item (63), Related U.S. Application Data, should read:
-- Continuation of application No. 10/540,060, filed on Jun. 22, 2005, now Pat. No. 7,616,785, filed as application No. PCT/JP2004/009698 on Jul. 1, 2004. --

Signed and Sealed this
Twenty-fifth Day of January, 2011

David J. Kappos
*Director of the United States Patent and Trademark Office*